(12) United States Patent
Knight et al.

(10) Patent No.: US 9,539,154 B2
(45) Date of Patent: Jan. 10, 2017

(54) MEDICAL DEVICE

(75) Inventors: David Philip Knight, Oxford (GB);
Stephanie Lesage, Oxford (GB)

(73) Assignee: OXFORD BIOMATERIALS LIMITED, Oxford, Oxfordshire (GB)

(*) Notice: Subject to any disclaimer, the term of this patent is extended or adjusted under 35 U.S.C. 154(b) by 45 days.

(21) Appl. No.: 14/238,307

(22) PCT Filed: Aug. 10, 2012

(86) PCT No.: PCT/GB2012/051962
§ 371 (c)(1),
(2), (4) Date: Jun. 2, 2014

(87) PCT Pub. No.: WO2013/021215
PCT Pub. Date: Feb. 14, 2013

(65) Prior Publication Data
US 2014/0288638 A1    Sep. 25, 2014

(30) Foreign Application Priority Data
Aug. 11, 2011   (GB) .................................... 1113856.7

(51) Int. Cl.
*A61F 2/06*   (2013.01)
*A61F 13/511*   (2006.01)
(Continued)

(52) U.S. Cl.
CPC ................ *A61F 13/511* (2013.01); *A61F 2/06* (2013.01); *A61L 27/3604* (2013.01);
(Continued)

(58) Field of Classification Search
CPC .............. A61F 2/06; A61F 2013/00238; A61F 2013/51139; A61F 13/511; A61F 13/5116
See application file for complete search history.

(56) References Cited

U.S. PATENT DOCUMENTS 7,635,755 B2   12/2009   Kaplan et al.
7,842,780 B2   11/2010   Kaplan et al.
(Continued)

FOREIGN PATENT DOCUMENTS

WO   WO 2005/094911   10/2005
WO   WO 2006/030182   3/2006
(Continued)

OTHER PUBLICATIONS

Aytemiz et al., "Small-Diameter Silk Vascular Grafts (3 mm Diameter) with a Double-Raschel Knitted Silk Tube Coated with Silk Fibroin Sponge" Advanced Healthcare Materials, 2013, 2, 361-368.
(Continued)

*Primary Examiner* — Christian Sevilla
*Assistant Examiner* — Seema Mathew
(74) *Attorney, Agent, or Firm* — Michael Best & Friedrich LLP

(57) ABSTRACT

The present invention relates to a medical device, particularly a vascular graft or an arteriovenous (AV) graft for haemodialysis. The medical device comprises a layer of porous silk fibroin matrix and a layer of knitted silk fibers. The invention further relates to processes of manufacture of such medical devices and methods of use of such devices.

20 Claims, 11 Drawing Sheets

(51) Int. Cl.
*A61L 27/36* (2006.01)
*A61L 27/50* (2006.01)
*A61L 31/00* (2006.01)
A61F 13/00 (2006.01)
A61M 1/36 (2006.01)

(52) U.S. Cl.
CPC .......... *A61L 27/507* (2013.01); *A61L 31/005* (2013.01); *A61F 13/5116* (2013.01); *A61F 2013/00238* (2013.01); *A61F 2013/51139* (2013.01); *A61M 1/3655* (2013.01)

(56) References Cited

U.S. PATENT DOCUMENTS

| | | | |
|---|---|---|---|
| 7,883,335 B2* | 2/2011 | Fischer | A61C 9/0033 433/136 |
| 7,922,487 B2* | 4/2011 | Fischer | A61C 9/0033 433/136 |
| 8,048,989 B2 | 11/2011 | Tsukada et al. | |
| 8,106,014 B2 | 1/2012 | Priestley et al. | |
| 8,178,656 B2 | 5/2012 | Kaplan et al. | |
| 8,309,689 B2 | 11/2012 | Yang et al. | |
| 8,313,764 B2* | 11/2012 | Steed | A61K 38/1841 424/443 |
| 8,361,617 B2 | 1/2013 | Kaplan et al. | |
| 8,501,172 B2 | 8/2013 | Kaplan et al. | |
| 8,530,625 B2 | 9/2013 | Kaplan et al. | |
| 8,614,293 B2 | 12/2013 | Kaplan et al. | |
| 8,623,398 B2* | 1/2014 | Altman | A61F 2/08 424/426 |
| 2004/0005363 A1 | 1/2004 | Tsukada et al. | |
| 2004/0199241 A1* | 10/2004 | Gravett | A61F 2/07 623/1.13 |
| 2006/0273279 A1* | 12/2006 | Kaplan | A61L 27/227 252/1 |
| 2007/0162121 A1* | 7/2007 | Tarrant | A61B 17/1146 623/13.12 |
| 2008/0009902 A1* | 1/2008 | Hunter | A61K 9/0024 606/228 |
| 2008/0096164 A1* | 4/2008 | Fischer | A61C 9/0033 433/136 |
| 2009/0171467 A1* | 7/2009 | Mann | A61F 2/30756 623/23.63 |
| 2011/0172394 A1* | 7/2011 | Knight | A61L 27/3604 530/353 |
| 2011/0177151 A1* | 7/2011 | Knight | A61L 27/3604 424/423 |
| 2011/0189773 A1 | 8/2011 | Altman et al. | |
| 2011/0224703 A1* | 9/2011 | Mortarino | A61F 2/0063 606/151 |
| 2011/0257665 A1* | 10/2011 | Mortarino | A61F 2/0063 606/151 |
| 2013/0190222 A1 | 7/2013 | Kaplan et al. | |
| 2015/0010630 A1* | 1/2015 | Llamas | A61L 27/227 424/484 |

FOREIGN PATENT DOCUMENTS

| | | |
|---|---|---|
| WO | WO 2009/133532 | 11/2009 |
| WO | 2010/036992 | 4/2010 |

OTHER PUBLICATIONS

Bhardwaj et al., "Freeze-gelled silk fibroin protein scaffolds for potential applications in soft tissue engineering" International Journal of Biological Macromolecules, 2011, 260-267.

Enomoto et al., "Long-term patency of small-diameter vascular graft made from fibroin, a silk-based biodegradable material" Basic Research Studies, 2010, 155-164.

Gao et al., "Improvements of anticoagulant activities of silk fibroin films with fucoidan" Front. Mater. Sci. China 2008, 2(2):221-227.

Liu et al., "Bilayered vascular grafts based on silk proteins" Acta Biomaterialia 9(11), 2013, 8991-9003.

Lovett et al., "Tubular silk scaffolds for small diameter vascular grafts" Organogenesis 6:4, 2010, 217-224.

Nakazawa et al., "Development of Small-Diameter Vascular Grafts Based on Silk Fibroin Fibers from Bombyx mori for Vascular Regeneration" Journal of Biomaterials Science, 2010, 12 pages.

Sato et al., "Small-diameter vascular grafts of Bombyx mori silk fibroin prepared by a combination of electrospinning and sponge coating" Materials Letters 64, 2010, 1786-1788.

Yagi et al., "Preparation of double-raschel knitted silk vascular grafts and evaluation of short-term function in a rat abdominal aorta" Japanese Society of Artificial Organs, 2011, 11 pages.

Zhao et al., "Preparation of braided silk as a tubular tissue engineering scaffold" Advanced Materials Research vols. 175-176, 2011, 95-99.

Zhong-Ling, "Physical and chemical characteristics of silk fibroin/fucoidan composite films" Journal of Clinical Rehabilitative Tissue Engineering Research, 2009, vol. 13, No. 8, 1589-1592.

International Search Report and Written Opinion for Application No. PCT/GB2012/051962 dated Oct. 8, 2012 (11 pages).

* cited by examiner

MEDICAL DEVICE

CROSS-REFERENCE TO RELATED APPLICATIONS

This patent application is a national stage filing under 35 U.S.C. 371 of International Application No. PCT/GB2012/051962, filed on Aug. 10, 2012, which claims foreign priority benefits to United Kingdom Patent Application No. 1113856.7, filed Aug. 11, 2011, which are incorporated herein by reference in their entireties.

The present invention relates to a medical device, particularly a vascular graft or an arteriovenous (AV) graft for haemodialysis. The medical device comprises a layer of porous silk fibroin matrix and a layer of knitted silk fibres. The invention further relates to processes of manufacture of such medical devices and methods of use of such devices.

According to the World Health Organization in 2010, cardiovascular diseases are the number one cause of mortality worldwide with 17.5 million deaths in 2005 and 48% of the total deaths in Europe in 2008 (British Heart Foundation). Atherosclerosis in small diameter arteries (<6 mm) is responsible for peripheral arterial disease (20% of global adult population affected) and is also associated with coronary heart diseases which account for 7.2 million of the cardiovascular related deaths. With 800,000 coronary bypass surgeries undergone globally each year (American Heart Association), the market for small artery substitutes is estimated to be a minimum of US$1.5 billion.

The gold standard replacement for long segments of lesioned small diameter arteries is mainly saphenous veins (patency of 60% after 5 years) or, where possible, the internal mammary arteries for better long term results (patency of over 90% after 10 years). However, as atherosclerosis is usually disseminated and common over the age of 30, adequate autologous veins are not available in 20% of patients and they are prone to further development of plaques with 50% of vein grafts closing after 10 years post-operation. Harvesting the veins also involves additional surgery resulting in delays for emergency non-elective cases. Therefore synthetic grafts have to be used as substitutes when no autologous vessels are available.

PET is mostly used in larger diameter arteries sustaining high pressures, but it is limited in its usefulness for small arteries (<5 mm internal diameter) due to its high thrombogenicity in low blood flow vessels. ePTFE vascular graft, which was developed by Robert W. Gore in 1975, is the most used material which is commercially available to replace small caliber arteries. Because of its highly electronegative fluorine atoms, ePTFE provides a low surface energy which minimizes the adhesion of platelets thus reducing the risk of thrombosis. Yet this property also impedes potential endothelial growth, preventing the use of a PTFE bypass in an infected environment. A mismatch of mechanical properties between the graft and the native artery is thought to induce anastomotic intimal hyperplasia in PTFE grafts which have a primary patency of 15% at 5 years below the knee. Therefore PET or PTFE grafts are a last resort and are unsuitable in the long term.

Haemodialysis is also currently increasing by 7-8% each year in the US. However, there are few grafts which are suitable for this use. Patients with renal failure need weekly dialysis of their blood. Haemodialysis access is usually obtained by bridging a patient's artery and a vein, and creating a high blood flow in the low arm, leg or neck. Ideally surgeons proceed with autogenous fistulae. However, many patients are not suitable candidates for these shunts and hence commercial grafts have to be used. The requirements for arteriovenous (AV) fistulae for haemodialysis are different in that the grafts may have to be punctured up to three times a week and they need to be particularly resistant to infections. The currently-used Dacron® and PTFE grafts have very low patency rates of under 50% for 12 months. In the US, an average of 1.8 surgical procedures per year/patient are required to maintain the dialysis access. Consequently, there is a need for a synthetic arteriovenous (AV) graft which could be punctured repeatedly and create less trauma than the current grafts and improve the patency Hence, there is a clear and unmet need for new artificial grafts, particularly in place of small caliber autologous grafts in peripheral or coronary bypass and arteriovenous fistulae or graft for haemodialysis access.

It is therefore an object of the invention to provide alternative and/or improved implantable materials, particularly small vascular grafts and arteriovenous (AV) grafts for haemodialysis access.

Silk fibres and silk solutions from the domestic silk worm, *Bombyx mori*, and some other silk worms have previously been used for the production of implantable materials. Silk's simple amino-acid composition, its inter- and intra-molecular hydrogen bonding and its high crystallinity makes it non-cytotoxic and provides it with low inflammatory and antigenic properties akin to materials which are already used clinically, such as collagen. Being soluble in various chaotropic agents, the *Bombyx mori* silk can be processed into different types of scaffolds and made porous in a controlled manner.

WO2005/094911 describes the production of composite materials comprising one or more silk elements in an acrylic or cross-linked protein matrix for use in surgical implants. WO2006/030182 describes the production of tubular medical devices comprising silk fibres set in a matrix of silk proteins for use in the regeneration of nerve cells. WO2009/133532 describes the production of regenerated silk fibroin solutions. Sato et al. (Materials Letters (2010), 64, 1786-1788) describes small diameter vascular grafts with a luminal layer of electrospun *Bombyx mori* fibroin fibres covered with an outer layer of *Bombyx mori* fibroin sponge. Lovett et al. (Organogenesis (2010) 6:4, 217-224) describes small diameter vascular grafts which have been prepared by gel spinning *Bombyx mori* fibroin on a rotating mandrel. Yagi et al. (Japanese Society for Artificial Organs (2011)) describes small diameter vascular grafts which have been prepared by coating a double-raschel knitted *Bombyx mori* silk tube with a mixed solution of PGDE and *Bombyx mori* fibroin solution.

Silk is one of the toughest known natural materials and it is unique in its combination of strength and elasticity. However, some silk filaments used in some embodiments of this invention may be up to 40% tougher and 60% more elastic than commercial silkworm silk. The presence of these RGD sequences and other reactive amino acid side chains also offers huge potential for chemical modification by providing numerous cross-linking sites along the molecule. This provides the possibility of significantly enhancing the graft's resistance to thrombogenecity and its attachment to endothelial cells.

The invention particularly relates to medical devices comprising a multilayered silk composite tube. These devices combine strong mechanical properties, good resistance to thrombogenecity and the high endothelial cell compatibility which are required for vascular applications.

In one aspect, the invention provides a medical device comprising a tubular body and a long axis, wherein the tubular body comprises:
(a) a layer of porous silk fibroin matrix; and
(b) a layer of knitted silk fibres,
wherein the luminal layer is a layer of porous silk fibroin matrix.

In a further aspect, the invention provides a medical device comprising a tubular body and a long axis, wherein the tubular body comprises:
(a) at least one layer of porous silk fibroin matrix; and
(b) at least one layer of knitted silk fibres,
wherein the luminal layer is a layer of porous silk fibroin matrix.

Preferably, the silk fibres of the knitted layer comprise fibroin proteins whose amino acid sequences comprise a plurality of RGD motifs.

In a further aspect, the invention provides a medical device comprising a tubular body and a long axis, wherein the tubular body comprises:
(a) a layer of porous silk fibroin matrix; and
(b) a layer of knitted silk fibroin fibres,
wherein the silk fibres of the knitted layer comprise fibroin proteins whose amino acid sequences comprise a plurality of RGD motifs.

In a further aspect, the invention provides a medical device comprising a tubular body and a long axis, wherein the tubular body comprises:
(a) at least one layer of porous silk fibroin matrix; and
(b) at least one layer of knitted silk fibroin fibres,
wherein the silk fibres of at least one of the knitted layers comprise fibroin proteins whose amino acid sequences comprise a plurality of RGD motifs. Preferably, the luminal layer is a layer of porous silk fibroin matrix.

In some embodiments, the silk fibres of the knitted layer are not obtained from mulberry silk worms or are obtained from non-mulberry silk worms or are obtained from wild silk worms.

The medical device is suitable for use as an implantable medical device, i.e. for use in vivo.

The medical device may, for example, be an arteriovenous (AV) graft for haemodialysis, a vascular graft, a bifurcation graft or an anastomosis device.

The vascular graft may be used in vivo as an artificial artery or vein, for example in lower limb revascularisation or coronary bypass operations. Preferably, the medical device is an arteriovenous (AV) graft for haemodialysis.

In some embodiments of the invention, the medical device is not an endoluminal device, e.g. the device is not a stent.

The medical device has a tubular body comprising a multilayered silk composite tube.

The layers of knitted silk fibres and porous silk fibroin matrix are generally concentrically disposed.

The tubular body will preferably have a substantially cylindrical form, having a long axis, an outer surface and an inner/luminal surface.

The tubular body will, in general, have a circular or substantially-circular cross-section, although other cross-sections (e.g. quadrilateral or other multisided shapes) may be used. Preferably, the tubular body has a circular cross-section. The external surface of the tubular body may be corrugated or of helical shape.

In some embodiments of the invention, the medical device comprises a tubular body having an internal diameter of from 0.5 mm to 30 mm, preferably from 0.75 to 10 mm, and more preferably from 2 to 6 mm.

In some preferred embodiments (e.g. for arteriovenous grafts), the internal diameter is 3 mm to 6 mm, more preferably about 5 mm or about 6 mm.

In some preferred embodiments (e.g. for lower leg grafts), the internal diameter is 2 mm to 6 mm, more preferably about 4 mm.

In other preferred embodiments (e.g. for coronary artery grafts), the internal diameter is preferably 2 mm to 4 mm.

The longitudinal axis may be of any suitable length. For example, the medical device may be produced and sold in the form of a long tube, allowing tubes of any desired length to be cut by the medical staff or surgeon involved with the implant.

In some embodiments of the invention, the longitudinal axis is 5 cm in length to 90 cm in length.

In some preferred embodiments (e.g. for arteriovenous grafts), the longitudinal axis is 5 cm to 40 cm or 5 cm to 60 cm, more preferably about 30 cm or about 50 cm.

In other preferred embodiments (e.g. for lower leg grafts), the longitudinal axis is 30 cm to 90 cm, more preferably about 70 cm.

The tubular body comprises (a) a layer of porous silk fibroin matrix.

The fibroin matrix may be formed from silk protein such as regenerated or redissolved silk protein. It may be obtained from mulberry or non-mulberry silk worms, or other sources.

In some embodiments of the invention, the silk fibroin protein is obtained from cocoon silks or silk filaments from the domesticated Mulberry Silkworm (*Bombyx mori*).

In other embodiments, the silk fibroin protein is obtained from non-mulberry silk worms or wild (non-domesticated) silk worms. Examples of such silk worms include *Antheraea* ssp., for example, *Antheraea assama, Antheraea militta, Antheraea pernyi, Antheraea yamamai* and *Philosamia* ssp. for example, *Philosamia Cynthia ricini* and *Philosamia Cynthia pryeri*.

The silk of other Saturnid moths such as those of the genus *Actias* or *Cecropia*, though not generally defined as wild silk worms, yield a closely similar silk and can be used in this invention as the source of the silk proteins.

The silk fibroin may also be produced by recombinant means, either directly as recombinant fibroin protein or derived from recombinantly-produced silk. Such fibroin may or may not have a wild-type fibroin amino acid sequence. The silk fibroin may also be produced by transgenic silk worms (e.g. those described in Nakazawa et al. J. Biomaterial Science (2010) 1-12).

In some preferred embodiments, the silk fibroin protein of the porous matrix does not have an amino acid sequence which comprises a plurality (e.g. 8 or more) of RGD motifs.

Preferably, the silk fibroin protein (of the porous matrix or otherwise) is obtained from mulberry silk worms, most preferably from *Bombyx mori*.

Silk comprises two main proteins, i.e. sericin and fibroin. In natural silk, fibroin forms the structural fibres in the silk, and sericin is the material surrounding the fibroin. Sericin sticks the fibres together in the cocoon.

Fibroin may be obtained from silk by degumming silk cocoons or silk filaments in order to remove or substantially remove the sericin protein. Methods of degumming silk and silk cocoons are known in the art (e.g. WO2009/133532, Sato et al. Materials Letters 64 (2010), 1786-1788).

Preferably, the fibroin is produced by the method disclosed in WO2009/133532 (Examples 1 and/or 2), the entire contents of which are incorporated herein by reference.

The fibroin used in the invention is preferably free or essentially free of sericin.

The fibroin porous matrix may be produced from a regenerated or redissolved fibroin solution.

As used herein, the term "regenerated" or "redissolved" refers to fibroin protein which has been obtained from silk in a process comprising the following steps: degumming the silk in order to remove silk sericin; dissolving in a chaotropic agent; removing the chaotropic agent by dialysis; and optionally concentrating the resulting fibroin solution. Additional steps can be added by way of example only to add additional components to the regenerated silk solution resulting in an aqueous silk fibroin solution. This silk fibroin solution has a largely amorphous protein structure, with limited amounts of beta-sheet structure.

The silk fibroin solution which is used for the porous fibroin matrix preferably has a concentration of 10-30%. When silk fibroin solution is used as an outer layer (e.g. to coat the knitted layer), it is preferably used at a concentration of 20-40%.

Degumming comprises the selective removal of sericin from the silk or silk cocoons and may use a proteolytic enzyme which cleaves sericin, but produces little or no cleavage of fibroin. (The proteolytic enzyme may comprise trypsin). Alternatively, the proteolytic enzyme may comprise proline endopeptidase or subtilisin. Degumming may use an enzyme solution in a buffer containing ammonium hydroxide.

Preferably, the fibroin solution is produced by a method comprising the steps:
  treating silk or silk cocoons with an ionic reagent comprising an aqueous solution of monovalent cations and monovalent anions, wherein the cations are selected from any one or more of the following: ammonium, potassium, rubidium, and the anions are selected from one or more of the following: hydroxide, chloride, bromide, nitrate; and
  degumming the treated silk or silk cocoons; or alternatively
  degumming silk or silk cocoons; and
  treating the degummed silk or silk cocoons with an ionic reagent comprising an aqueous solution of monovalent cations and monovalent anions, wherein the cations are selected from any one or more of the following: ammonium, potassium, rubidium, and the anions are selected from one or more of the following: hydroxide, chloride, bromide, nitrate.

In order to produce a fibroin matrix from the fibroin solution, the solution is gelled.

Preferably, the silk fibroin solution is gelled by treating the fibroin solution with an aqueous solution of a gelling reagent or by a combination of gelling reagents, such as, for example, an acid. The gelling reagent may, for example, comprise glacial acetic acid vapour.

In some embodiments, the regenerated silk fibroin solution is gelled to form a hydrogel. In other embodiments, the gelled material is subjected to one or more freezing cycles. In other embodiments, the gelled material is subjected to ethanol treatment.

The gelled silk fibroin solution is preferably treated with ethanol to induce the formation of beta sheet and to render the scaffold non-soluble.

The matrix is largely comprised of intercommunicating pores. Preferably, the pores cover from approximately 10% up to approximately 80% of a cross-section of the material. Preferably, the pore sizes range from approximately 5 µm to approximately 1000 µm in diameter. The pore size ranges preferably between 10 µm and 50 µm or 10 µm and 200 µm. Preferably, the fibroin is circumferentially orientated in the pore walls.

The radial thickness of the layer of porous silk fibroin matrix is preferably 0.1 mm to 1.5 mm, more preferably 0.1 to 1.0 mm and most preferably 0.4 to 0.7 mm or 0.4 to 1.0 mm.

In other embodiments, the radial thickness of the layer of porous silk fibroin matrix is preferably 50% to 90% of the radial thickness of the wall of the medical device.

In some embodiments of the invention, the tubular body comprises a luminal layer of porous silk fibroin which does not comprise silk fibres or knitted silk fibres. More preferably, the tubular body comprises a luminal layer of porous silk fibroin which is at least 0.1 mm to 1.5 mm, more preferably 0.1 to 1.0 mm and most preferably 0.4 to 0.7 mm or 0.4 to 1.0 mm thick and which does not comprise silk fibres or knitted silk fibres.

The layer of porous silk fibroin matrix may be incorporated into the medical device by any suitable means.

For example if the porous layer is adjacent to the lumen, i.e. on the inside of the graft, the porous layer may be formed by dipping a tubular former into a regenerated or redissolved fibroin solution, or spraying or painting the tubular former with a regenerated or redissolved fibroin solution. More preferably, a regenerated or redissolved fibroin solution may be cast or moulded over a tubular former. A regenerated/redissolved fibroin solution may be injected in a tubular mould containing a rod centered in the body of the mould.

In some embodiments of the invention, the tubular former may or may not already be covered with one or more layers of knitted silk fibres. In some embodiments of the invention, a knitted silk fibre layer may be coated on a rod, preferably with fibroin solution and left to dry.

In some embodiments, the outer surface of the tubular former may be coated with material to form the luminal surface of the device before covering it with one or more layers of knitted silk fibres.

In some embodiments of the invention, the tubular former is made of silicone or plastic. In some preferred embodiments of the invention, the tubular former is made of plastic or magnaplated metal. In some other embodiments of the invention, the tubular former is porous to allow the gelling of the silk conduit through the mould walls. In some other embodiments of the invention, the tubular former comprises a dialysis membrane to allow gelling of the silk conduit through the dialysis membrane wall.

The tubular body also comprises (b) a layer of knitted silk fibres. The silk fibres of the knitted layer comprise fibroin proteins. The knitted layer may be made of single fibres or may be made of bundles of fibres twisted together.

The silk fibres of the knitted layer may comprise fibroin proteins from Mulberry silk worms such as *Bombyx mori* silk or from non-Mulberry silk worms or from wild silk worms.

In some embodiments the tubular body or its luminal lining may also comprise chopped or micronized silk fibres.

Preferably, the silk fibres of the knitted layer or the chopped or micronized silk fibres comprise fibroin proteins whose amino acid sequences comprise at least eight repeats of the triplet RGD. The eight repeats of the triplet RGD may be located immediately adjacent to turns or predicted turns of a structure of the principal silk protein. This is advantageous because this sequence, when next to a turn, specifically recognises and holds the fibronectin binding site of integrin molecules anchored to the surface of most metazoan cell types. This leads to excellent cell adhesion and advantageous changes in cell physiology including polarisation of function, cell differentiation and changes in the cell cycle; and encourages cell migration onto the medical device.

The presence of these RGD sequences and other reactive amino acid side chains also offers potential for chemical modification by providing numerous cross-linking sites along the silk molecule. The silk's resistance to thrombogenicity and attachment to endothelial cells may be enhanced by combining it with one or more anticoagulant agents such as heparin, sulfonates, fucoidan or water-soluble polymers such as 2 methacryloyloxyethyl phosphorylcholine or s-carboxymethyl keratine. The addition of such anti-thrombogenic agents could modify the devices of the invention to render them more suitable for vascular applications. Additionally, one or a combination of anti-thrombogenic agents may be incorporated non-valently into one or more layers of regenerated silk protein on the luminal surface or within the wall of the device. For example, a first outer layer of porous silk fibroin matrix may be produced by injecting concentrated silk fibroin between the outer knitting structure and a larger former. The conduit once gelled may be reintroduced in the mould and a second internal layer of less concentrated silk fibroin and the anti-thrombogenic agent may be injected between the first conduit and a smaller former to add a more internal layer to the conduit.

In other embodiments, one or more of the knitted silk fibre layers may be coated with a protein, polypeptide or peptide comprising a plurality (e.g. 3 or more) RGD sequences.

In another embodiment, an antiproliferative agent (e.g. pachitaxel, rapamycin) may be incorporated into the regenerated silk fibroin at one or both of the ends of the device to prevent stenosis by hyperplasis.

In other embodiments, the tubular body comprises (b) a layer of knitted silk fibres, wherein the silk fibres of the knitted layer are not obtained from mulberry silk worms or are obtained from non-mulberry silk worms or are obtained from wild silk worms. In other embodiments, the regenerated silk protein comprising the luminal layer or matrix of the device is produced from non-mulberry or wild silk worm silk fibres.

As used herein, the term "silk fibres obtained from non-mulberry silk worms" refers to silk fibres which are not obtained from mulberry silk worms such as *Bombyx mori*.

In particular, the silk fibres may be obtained from wild (i.e. non-domesticated) silk worms. Examples of such silk worms include *Antheraea* ssp., for example, *Antheraea assama, Antheraea militta, Antheraea pernyi, Antheraea yamamai*, and *Philosmia* ssp. for example, *Philosamia Cynthia ricini* and *Philosamia Cynthia pryeri*.

The silk fibres may also be obtained from other Saturnid moths such as those of the genus *Actias* or *Cecropia*. Although these are not generally defined as wild silk worms, they yield a similar silk and can be used in this invention as the source of the silk fibres.

The use of non-mulberry silk has a number of advantages including improved mechanical properties and better cytocompatibility. Non-mulberry silks are also biodegradable (thus allowing absorption of the device by the body over time); and the presence of RGD sequences encourages invasion of host cells.

The silk fibres may also be obtained from transgenic silk worms (e.g. such as those described in Nakazawa et al. J. Biomaterial Science (2010) 1-12).

Fibroin proteins from the domesticated silk moth *Bombyx mori* do not have amino acid sequences which comprise a plurality of RGD motifs.

As used herein, the term "knitted" refers to a structure wherein loops of silk fibres are intertwined.

The knitted layer consists of a plurality of consecutive loops called stitches, arranged in rows, wherein, as each row progresses, a new loop is pulled through an existing loop. Longitudinally along the tube, each stitch is suspended from the one above it.

The skilled person would clearly understand that the term "knitted" does not include braided structures or plaited structures or woven structures. Braiding or plaiting involves twisting threads together into cloth. In contrast to weaving, the threads in the knitted structure are not straight, and running parallel either lengthwise or crosswise.

The loops in a knitted fabric can be stretched easily in different directions, which gives knitting much more elasticity than woven, plaited or braided fabrics.

The knitted layer may be formed on the porous layer or on a suitable former, i.e. knitted in situ, or the knitted layer may be produced separately and then combined with the porous layer.

The silk fibres may be washed with a solution of a chelating agent, for example, ethylene diamine tetra-acetic acid (EDTA) sodium salt to remove possible contaminants, such as transition metal ions which may be toxic. Other chelating agents could also be used.

The silk fibres which are used in the knitted layer are generally degummed silk fibres.

The knitted silk fibres are natural silk fibres which have preferably been degummed, but which have not been reconstituted or redissolved.

The silk fibres generally have a diameter of 2-30 μm. Twisted fibres generally have a diameter of 5-300 μm.

The knitted layer may comprise silk fibres of the same or different linear densities. For example, fibres of different densities may be used in certain areas of the device in order to enhance the flexibility of those areas.

In other embodiments, defined areas of the device may have different number of knitted loops per unit area. This may be desired in order to enhance or reduce the flexibility of the device in certain areas, or for other purposes.

If desired, the device may be made of a suitable stiffness which prevents kinking of the tubular body when it is bent. This is particularly desirable for haemodialysis grafts in order to maintain patency.

For example, the tubular body may comprise one or more annulate, helical, threaded, spiral, grooved, crimped or corrugated supports. For example, one or more of the layers may have, partially or completely, an annulate, helical, threaded, spiral, grooved, corrugated or crimped form or profile. In some embodiments, the annulate, helical, threaded, spiral, grooved, corrugated or crimped form or profile of one or more of the layers is in the middle section of the tubular body. This allows greater flexibility in this middle section. Preferably, the supports or the form or profile is helical.

The layer of porous silk fibroin matrix is generally formed from a regenerated silk solution and hence it may readily be moulded into a desired shape.

Hence in one embodiment, the layer of porous silk fibroin matrix is moulded, partially or completely, into an annulate, helical, threaded, spiral, grooved, corrugated or crimped form or profile, preferably into a helical form or profile.

For example, fibroin solution may be injected into a mould having the desired shape of the porous layer, and the solution may then be gelled. The gelled porous matrix may then be removed from the mould.

Crimping may be introduced in the matrix by injecting the silk in a mould where the inner wall has the spiral shape of a screw. The spiral preferably has grooves of between 0.5 and 3 mm in depth, more preferably about 1.5 mm in depth. The mould may be produced in two parts so that the crimped moulded silk device may be taken out easily without damaging the grooves.

In other embodiments, the knitted layer may take an annulated, helical, threaded, spiral, grooved, corrugated or crimped form or profile. For example, the knitted layer may be placed on a mould of a desired shape, and then coated with a layer of silk fibroin solution (preferably diluted).

Medical devices having such a form or profile are kink-resistant. As used herein, the term "kink-resistant" means that the medical device (e.g. pressurised at 0.16 bar of water) may be wrapped around a cylindrical mandrel of 4 mm diameter or greater without kinking being observed.

Pressure may optionally be applied onto the knitted layer in order to promote its drying in the form or profile of the mould. The pressure may take the form of a silk thread or suture which is wound over the knitted layer in order to compress it into the mould.

Once dried, the knitted layer may be removed from the mould, wherein the knitted layer will retain the form or profile of the mould.

In one embodiment, the crimping or other form or profile may be introduced in the knitted structure by introducing a screw-shaped rod into a knitted tube, winding a silk thread around the silk knit and along the groove to compress the knitted structure into the crimped shape. A thin coating of silk fibroin could then be applied on the knitted tube and subsequently left to dry. The silk thread initially maintaining the crimp shape would be unwound and the knitted tube un-screwed off the rod, still maintaining the crimped shape. It could then be introduced in a mould (the mould itself being straight or with grooves as described above), and the regenerated silk fibroin solution would be introduced in the mould and gelled in a usual manner. The mould may then be left between 0° C. and −5° C. for 10 minutes to 12 hours in order to enhance the interphase between the previously-dried coated knit and the fresh regenerated silk. The mould could then be gelled in a usual manner. When gelled, the knitted layer within the matrix will have maintained a crimped aspect.

In another embodiment, the silk thread initially maintaining the crimped shape is a silk suture of 0.2 mm to 1 mm in diameter, preferably about 0.4 mm in diameter, and it is permanently left on the helical knitted structure, sealed onto the knitted structure by the silk fibroin solution to increase the hoop strength of the graft. The suture may be left on the entire length of the graft, or only in the middle portion of the graft to provide flexibility in the central region without increasing the circumferential stiffness along the whole graft.

In preferred embodiments, therefore, one or more layers of porous silk fibroin matrix and/or one or more layers of knitted silk fibres are partially or wholly present in an annulate, helical, threaded, spiral, grooved, corrugated or crimped form or profile. In some preferred examples of this embodiment, one or more silk threads or sutures are engaged in the grooves of the annulate, helical, threaded, spiral, grooved, corrugated or crimped form or profile on the outer, i.e. non-luminal, side of the knitted layer(s). The silk thread or suture may be braided.

The tubular body of the medical device comprises: (a) a layer of porous silk fibroin matrix; and (b) a layer of knitted silk fibres.

In some embodiments, the inner (luminal) layer is a layer of porous silk fibroin matrix.

In other embodiments, the inner (luminal) layer is a layer of knitted silk fibres, optionally coated with silk fibroin matrix.

In yet other embodiments, the tubular body comprises: (a) an inner layer of porous silk fibroin matrix, and (b) an outer layer of knitted silk fibres.

In yet other embodiments, the tubular body comprises: (a) an outer layer of porous silk fibroin matrix, and (b) an inner layer of knitted silk fibres.

In yet other embodiments, the tubular body comprises: (a) an inner layer of porous silk fibroin matrix, (b) an intermediate layer of knitted silk fibres, and (c) an outer layer of knitted silk fibres.

In yet other embodiments, the tubular body comprises: (a) an outer layer of porous silk fibroin matrix, (b) an intermediate layer of knitted silk fibres, and (c) an inner layer of knitted silk fibres.

In yet further embodiments, the tubular body comprises: (a) an inner layer of porous silk fibroin matrix; (b) an intermediate layer of knitted silk fibres; and (c) outer layer of porous silk fibroin matrix.

In yet further embodiments, the tubular body comprises: (a) an inner layer of knitted silk fibres; (b) an intermediate layer of porous silk fibroin matrix; and (c) outer layer of knitted silk fibres.

The outer layer or layers of knitted silk fibres may be embedded in or coated with a porous silk fibroin matrix.

In a preferred embodiment, the tubular body comprises: (a) an inner layer of porous silk fibroin matrix; (b) an intermediate layer of knitted silk fibres, and (c) an outer layer of knitted silk fibres, wherein the knitted silk fibres are embedded in or coated with a porous silk fibroin matrix.

In another preferred embodiment, the tubular body comprises: (a) an inner layer of knitted silk fibres, and (b) an outer layer of knitted silk fibres, wherein the knitted silk fibres of one or both knitted layers are embedded in or coated with a porous silk fibroin matrix.

In yet further embodiments, the innermost layer or the outermost layer, or both innermost and outermost layers of the tubular body are coated with an additional impermeable silk fibroin layer (which may be obtained with an acetic acid treatment for example).

As used herein the term "layer" encompasses both a complete layer (i.e. one which covers the complete circumference along the whole length of the device) and partial layers. Preferably, the layer covers at least 50%, more preferably at least 60%, 70%, 80% or 90% of the external area of the device, and most preferably at least 95% or 99% of the external area of the device. This applies independently to each of the porous layer(s) and the knitted layer(s).

The walls of the tubular body may have a total thickness of from about 250 μm to about 1500 μm, preferably from about 300 μm to about 800 μm, and most preferably of around 400 μm to 700 μm.

The layers of the tubular body may be cross-linked either within themselves and/or between the layers. Preferably, one or more layers are wholly or partially inter- or intra-cross-linked to make the layer(s) and/or the device substantially non-degradable or substantially non-biodegradable. The degree of cross-linking may be used to control the extent or rate of degradation in vivo.

Cross-linked may be performed using a cross-linking agent, e.g. formaldehyde vapour, glutaraldehyde, polyglutaraldehyde, hexamethylene diisocyanate, formaldehyde carbodiimide, genipinm, citrate ions, ribose or glyoxal. Ultraviolet or ionising radiation can also be used to cross-link the silk fibres and/or regenerated silk protein of the device.

Alternatively, one or more of the layers may be cross-linked by heating in substantially dry formaldehyde vapour, e.g. generated by heating paraformaldehyde in a sealed container to 80-100° C. for 5 minutes to 3 hours.

In a further embodiment, one or more layers of the device may independently additionally comprise one or more biologically active substances. The substances may be selected from the group consisting of nitric oxide or nitrogen monoxide, growth factors, cytokines, antibiotics, immunosuppressants, steroids, non-steroidal anti-inflammatory drugs (NSAIDs), anti-microbial or infection resistant substances or coatings.

Other biologically-active substances include, but are not limited to, cAMP enhancers (e.g. rolipram or db-cAMP) to promote regeneration, molecules that reduce scar formation (e.g. TFG-β, antisera and/or chondroitinase), or molecules that reduce myelin inhibition (e.g. anti-Nogo treatments).

In some embodiments, one or more layers of the device comprise one or more anti-thrombotic agents, preferably the luminal layer. Examples of suitable anti-thrombotic agents include paclitaxel, heparin, warfarin, aspirin and clopidogrel.

Fucoidan is known to have anti-coagulant properties. In other embodiments of the invention, therefore, one or more layers of the device comprise fucoidan. For example, fucoidan may be blended with the regenerated or redissolved fibroin solution before production of the porous fibroin layer. In other embodiments, the fucoidan may be cross-linked to the fibres, e.g by chemical cross-linking agents or radiation, or it may be blended with regenerated silk fibroin used to coat the knitted layer.

In yet other embodiments, the fucoidan may be depyrogenated.

The invention also provides a process of manufacturing a medical device comprising the steps forming a tubular body comprising: (a) a layer of porous silk fibroin matrix; and (b) a layer of knitted silk fibres, wherein the luminal layer is a layer of porous silk fibroin matrix.

The invention further comprises a process of manufacturing a medical device comprising the step forming a tubular body comprising: (a) a layer of porous silk fibroin matrix; and (b) a layer of knitted silk fibres, wherein the silk fibres of the knitted layer comprise fibroin proteins whose amino acid sequences comprise a plurality of RGD motifs.

In some embodiments, the process comprises the steps:
(i) inserting one or more tubular layers of knitted silk fibres onto a cylindrical former;
(ii) applying a coating of regenerated or redissolved silk fibroin solution onto the knitted layer(s) and allowing the coating to dry;
(iii) removing the coated knitted layer(s) from the former;
(iv) inserting the coated knitted layer(s) into a mould,
(v) injecting regenerated or redissolved silk fibroin into the mould, and allowing the silk fibroin to set, such that a tubular body is formed in the mould comprising concentric layers of one or more layers of knitted silk fibres and one or more layers of porous silk fibroin matrix.

The former may, for example, be a rod, cylinder or tube having an external radial diameter of the desired internal radial diameter of the knitted layer.

In other embodiments, the process comprises the steps:
(i) inserting one or more tubular layers of knitted silk fibres onto a former having a annulate, helical, threaded, spiral, grooved, corrugated or crimped form or profile;
(ii) winding a silk thread or suture over the knitted silk fibre layer(s) at a tension such that the silk thread or suture and silk fibre layer(s) engage within the grooves of the former (i.e. to hold the knitted layer(s) in close proximity with the former);
(iii) applying a coating of regenerated or redissolved silk fibroin solution onto the knitted layer(s);
(iv) allowing the coating of regenerated or redissolved silk fibroin solution to dry (such that the knitted layer(s) retain the shape of the former);
(v) removing the coated knitted layer(s) from the former;
(vi) inserting the coated knitted layer(s) into a mould;
(vii) injecting regenerated or redissolved silk fibroin into the mould, and allowing the silk fibroin to set, such that a tubular body is formed in the mould comprising concentric layers of one or more layers of knitted silk fibres and one or more layers of porous silk fibroin matrix. The order or steps (ii) and (iii) as given above may be reversed.

The mould provides an internal surface which defines the outer (i.e. external) surface (i.e. external diameter) of the tubular body. For example, the mould may comprise a bore whose internal surface defines the outer surface of the tubular body. Within the bore may be a cylindrical member running generally coaxially thereto, whose outer surface defines the internal surface of the tubular body, i.e. its internal diameter.

The mould may be made of a metal coated with a lubricious coating to prevent adhesion of the silk to the mould. Preferably, the mould may be magnaplated.

If the silk solution is injected in one end of the mould, vacuum may be applied at the other end of the mould prior to silk injection to reduce air bubbles forming in the graft and prevent undesired porosity in the graft. The mould may be placed vertically with the vacuum created at the top end of the mould and the silk injected in the bottom end of the mould to further reduce introduction of air in the mould. The silk may be injected in the mould through a large passage to reduce pressure and trapping of air.

The moulded device is preferably left for 10 minutes to 12 hours, preferably for about 60 minutes, to set in order to enhance the interphase between the dried coated knit and the freshly injected regenerated matrix. Preferably, the moulded device is kept at about 0° C. to −5° C. during this time.

The moulded device is preferably then frozen, most preferably at about −20° C. or about −80° C., e.g. for 5 to 60 minutes.

After or during production (preferably after moulding), the proteins in the medical device may be gelled. For example, the device may be exposed to acetic acid solution or glacial acetic acid vapours or a combination of acetic acid and polyethylene glycol, e.g. for between 1 minute and 12 hours. Preferably, the device is exposed for between 20 minutes and 60 minutes.

The device may then be frozen for at least 5 minutes, preferably between 10 minutes and 10 hours, most preferably between 20 minutes and 60 minutes.

The device may be treated with alcohol, preferably ethanol, in order to cross-link the gelled proteins. This changes the amorphous fibroin into beta sheet structures. Preferably, the device is immersed in ethanol of a concentration of more than 20%, more preferably between 30% and 70%.

In some processes of the invention, the process additionally comprises cross-linking one or more of the layers or cross-linking one layer to one or more of the other layers.

The invention further provides a medical device comprising a tubular body obtained or obtainable by a process of the invention.

For implantation, an appropriate diameter device is selected according to the diameter of the artery or vein to be repaired. An appropriate length of the device may be cut off with a sharp blade or other instrument. In one embodiment, the device is held in place by one or more sutures. In another embodiment, the device can be held in place with fibrin glue.

The device may be provided in dehydrated or lyophilised form and subsequently rehydrated by the user, or it could be provided in hydrated form. For example, the device may be soaked for five minutes to five hours in an appropriate physiological saline solution before use. Alternatively, the device could be provided hydrated and sterilised, e.g. in a phosphate buffer solution.

In some embodiments, the device may additionally comprise cells, for example, vascular cells, e.g. endothelial cells, HUVECs and/or smooth muscle cells.

The cells may be endogenous cells from the patient into whom the device is to be implanted, or the cells may be exogenous cells from an external source, e.g. cells grown in culture. In other words, the cells may be autologous or non-autologous with respect to the immune system of patient to be treated.

The invention further provides a medical device of the invention for use in a method of therapy, treatment or surgery.

The invention also provides a medical device of the invention for use as a vascular graft in a method of surgery. Preferably, the method of surgery is the replacement of a lower limb arteries (example femoral artery) or vein, or coronary artery or vein.

The invention also provides a medical device of the invention for use in a coronary bypass operation.

The invention also provides a medical device of the invention for use as an arteriovenous (AV) graft for haemodialysis.

The invention further provides a method of replacing a diseased artery or vein in a patient comprising removing all or part of a diseased artery or vein in that patient and replacing all or part of the diseased artery or vein with a medical device of the invention.

The invention also provides a method of treating a patient with coronary heart disease, comprising replacing all or part of one or more of the patient's coronary arteries or veins with a medical device of the invention.

The invention also provides a method of preparing a patient for haemodialysis, comprising inserting an arteriovenous (AV) graft of the invention between one of the patient's arteries and one of the patient's veins.

The invention further provides a method of haemodialysis, comprising the steps:
(i) extracting blood from a patient through an arteriovenous (AV) graft of the invention,
(ii) dialysing the extracted blood, and optionally (iii) returning the dialysed blood to the patient.

Preferably, the graft of the invention connects one of the patient's arteries to one of the patient's veins.

BRIEF DESCRIPTION OF THE FIGURES

FIG. 12 shows the mould when closed. FIG. 13 shows the inside of the mould. Hinges, latches and dowels hold the two parts of the mould perfectly aligned. A gasket along the inside of the mould prevents leakage after injection of the silk. Threaded inserts on each end allow attachment of luer syringes for injection of the silk. Jacking screws help easy opening of the mould once frozen.

EXAMPLES

Figure 1:
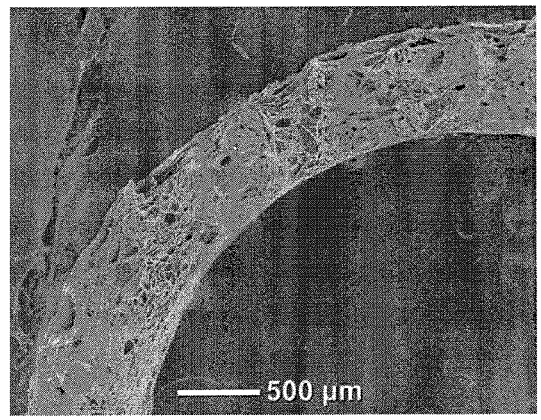
FIGS. 1-3 show scanning electron microscopy (SEM) photos of 3 different straight silk conduits obtained by the moulding process where the wall thickness is maintained regular and controlled by adjusting the internal diameter of the plastic mould. An SEM Neo Scope Jeol at 10 kV-15 kV was used for these photos.
Figure 2:
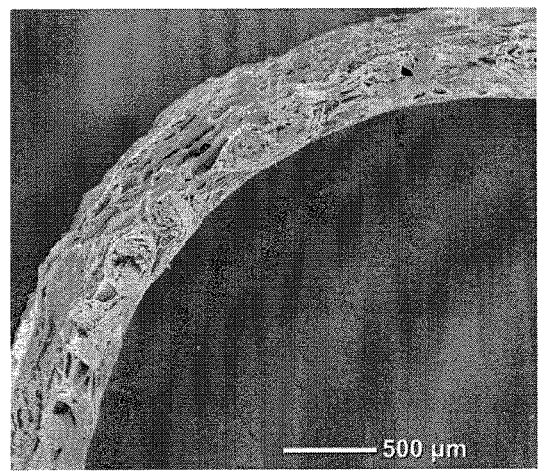
Figure 3:
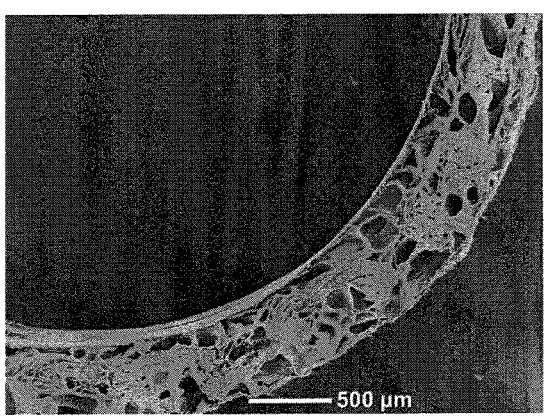
Figure 4:
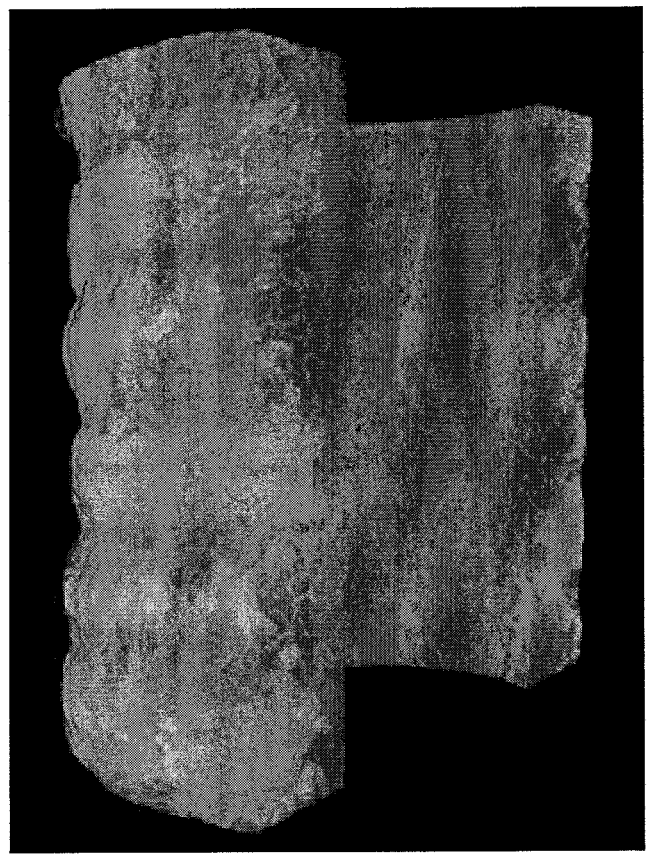
FIGS. 4-5 show microCT photos of the kink resistant helical design obtained using a helical shaped former to prepare the outer knit and integrating a permanent silk suture around the knit. The MicroCT photos were obtained from AccelLab in Quebec.
Figure 5:
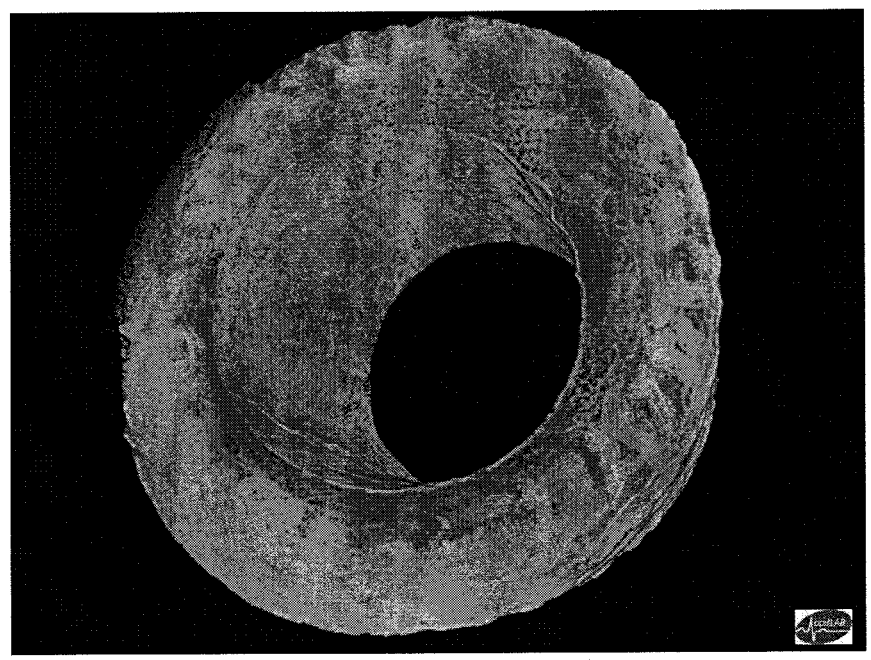

The present invention is further defined in the following Examples, in which parts and percentages are by weight and degrees are Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions. Thus, various modifications of the invention in addition to those shown and described herein will be apparent to those skilled in the art from the foregoing description. Such modifications are also intended to fall within the scope of the appended claims. The disclosure of each reference set forth herein is incorporated herein by reference in its entirety.

Example 1

Preparation of Porous Regenerated Silk

Silk cocoons or silk bave 20-37 denier of *Bombyx mori* were first washed with a dilute solution of ethylene diamine tetra-acetic acid (EDTA) sodium salt to remove possible contaminants, such as transition metal ions which may be toxic. The silk was then degummed. This was achieved by treatment of the silk using a protease, for example subtilisin. The enzyme was washed out after treatment. The degummed fibroin was dissolved in aqueous 6.3M lithium bromide solution. The lithium bromide was removed by exhaustive dialysis against distilled water at 40° C. The dialysate was concentrated within the dialysis tubes by evaporation or reverse dialysis.

Example 2

Preparation of Knitted Silk Fibres

Silk cocoons or silk bave 20-37 denier of wild silkworms were first washed with a dilute solution of ethylene diamine tetra-acetic acid (EDTA) sodium salt to remove possible contaminants, such as transition metal ions which may be toxic. The silk was then degummed. This was achieved by a repeated treatment of the silk using a protease, for example a subtilisin, but other mild proteolytic enzymes may also be used. The enzyme was washed out after treatment.

Example 3

Preparation of Knitted Layer

The knitted layers were prepared using a Semel s.n.c. (Italy) knitting machine, model no. L250T. This knitting machine has interchangeable cylinders which dictate the maximum number of needles used and hence the diameter of the knitted tubes produced. Four interchangeable cylinders were used, allowing the production of tubes ranging from 3 mm to 15 mm in diameter:
Cyl-12N: 12 needles/gauge 20—diameter up to 4.4 mm
Cyl-16N: 16 needles/gauge 20—diameter up to 5.8 mm
Cyl-18N: 18 needles/gauge 20—diameter up to 6.6 mm
Cyl-32N: 32 needles/gauge 20—diameter up to 12 mm Example 4

Production of the Vascular Graft

The knitted silk fibre layer was placed on a helical former of the appropriate diameter. A braided silk strand was wound around the knit on the helical former and the braid+knit were slightly coated with regenerated silk fibroin and subsequently dried. The former was then removed and the dried knitted silk fibres layer inserted in a tubular mould containing a central rod of the diameter of the desired internal diameter of the final conduit. The regenerated silk fibroin was injected in the mould containing the central rod and inside the dried knitted silk fibres. The mould was left between 0° C. and −5° C. for 60 minutes, so that the coating of the knitted fibres blended with the regenerated silk fibroin in the mould. The mould was then left in the freezer at −20° C. for 10 minutes or more or at −80° C. for 5 minutes. The whole conduit was taken out of the mould and left to gel in acetic acid solution for between 20 and 60 minutes. The conduit was then frozen for 20-60 minutes and subsequently left in ethanol of a concentration of between 30% and 50%. After the conduit was rinsed, it was dipped in regenerated silk and then left in acetic acid for 30 minutes before it was stored again in ethanol 50% to add an impermeable layer.

Figure 12:
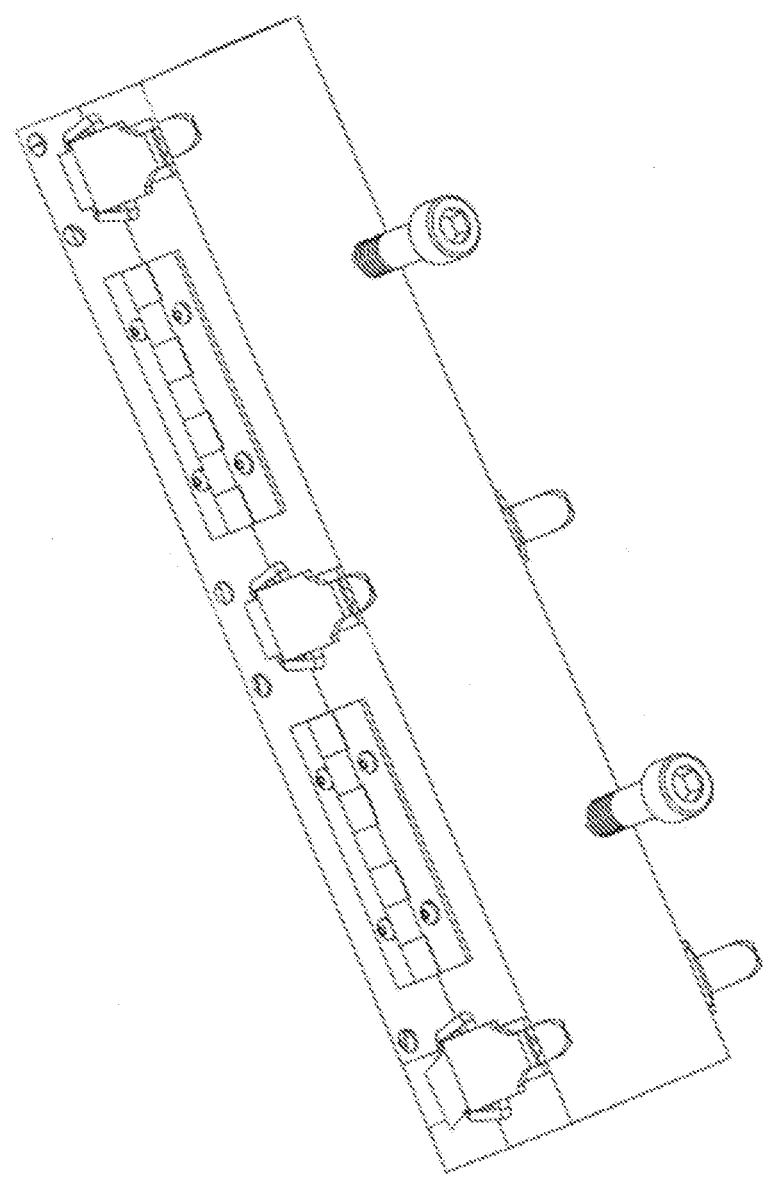
FIGS. 12 and 13 show an example of a two part magnaplated mould.
Figure 13:
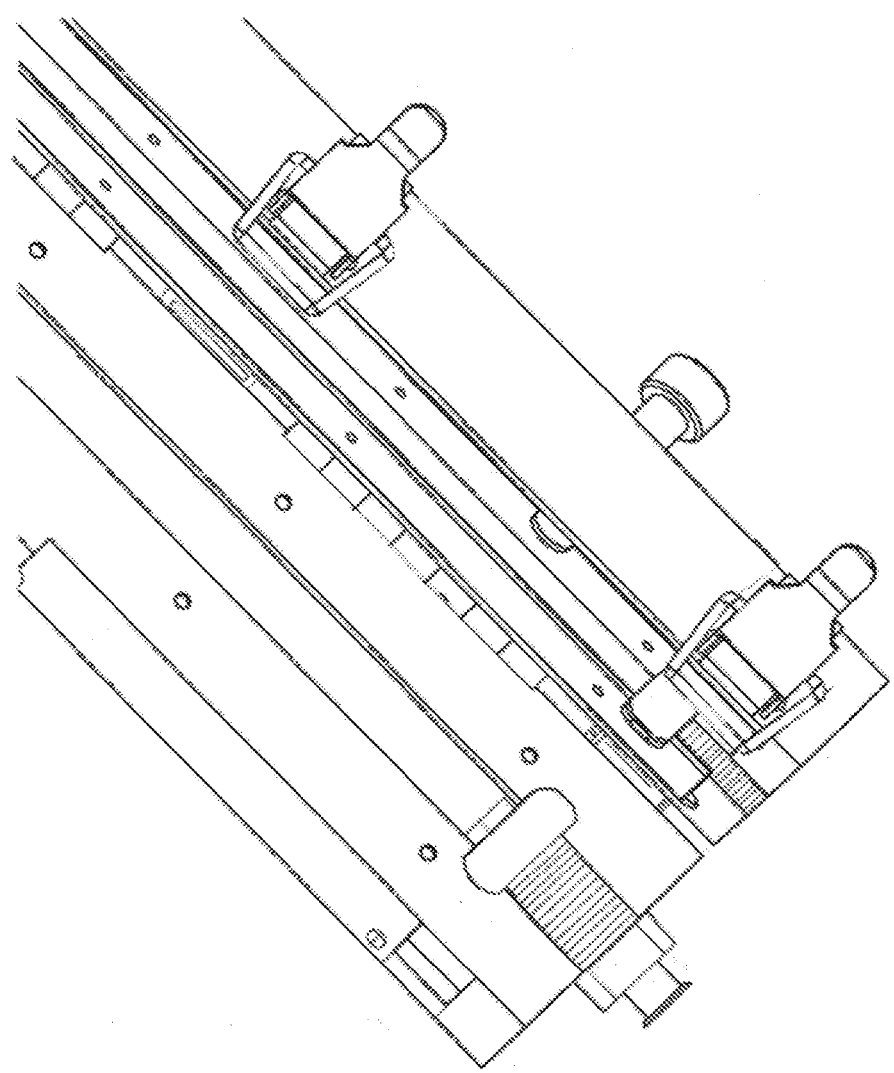
Figure 14:
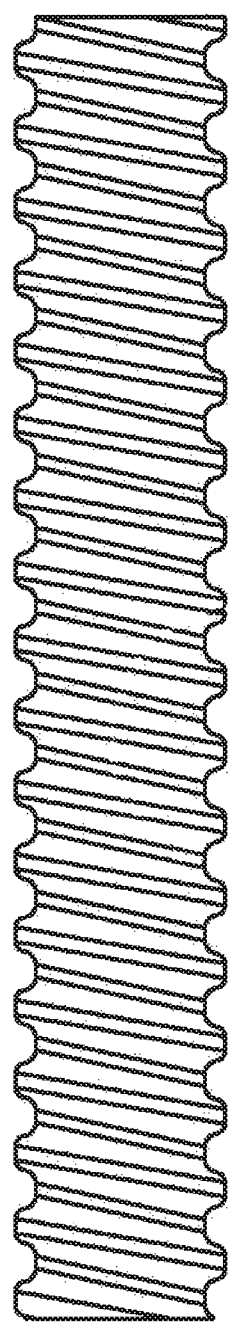
FIG. 14 shows an example of a magnaplated helical former.

FIGS. 12 and 13 show an example of a two part magnaplated mould. FIG. 12 shows the mould when closed. FIG. 13 shows the inside of the mould. Hinges, latches and dowels hold the two parts of the mould perfectly aligned. A gasket along the inside of the mould prevents leakage after injection of the silk. Threaded inserts on each end allow attachment of luer syringes for injection of the silk. Jacking screws help easy opening of the mould once frozen. FIG. 14 shows an example of a magnaplated helical former.

Examples of the tubes of the invention are shown in FIGS. 1-7. These illustrate particularly the regular wall thicknesses which are obtainable using the invention.

Example 5

Kink Resistance Testing Protocol

The kink resistance of the different conduits was tested using various sized mandrels and following the ANSI standards. For each sample, the grafts were wrapped around cylindrical mandrels of decreasing sizes until a slight kink was observed. The radius of the smallest cylindrical mandrel used without kinking was recorded for each graft. The test was done both non-pressurized (and hydrated in the case of the silk grafts) and with the grafts pressurized at 0.16 bar of water. Both silk and commercial grafts were compared. The results are shown in FIGS. 6-8.

Figure 6:
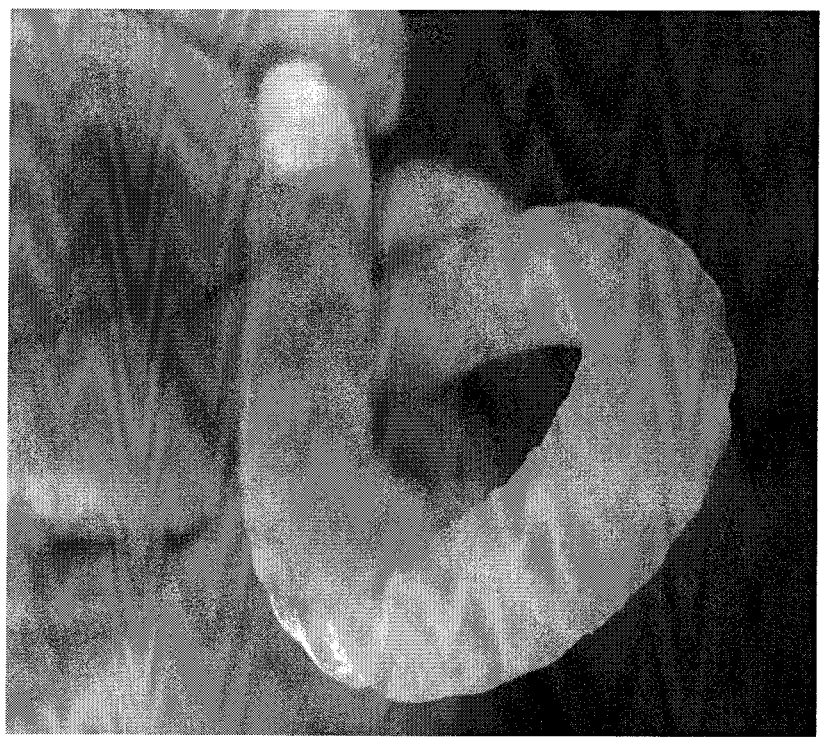
FIGS. 6-7 show the flexibility of the kink resistant helical design silk conduits. Photos were taken with a digital camera Sony Cyber-shot 7.2 mega pixels.
Figure 7:

FIGS. 6 and 7 show the kink resistance of the conduits produced using the helical mandrel and the silk suture wrapped around to reinforce the hoop strength of the conduit.

Figure 8:
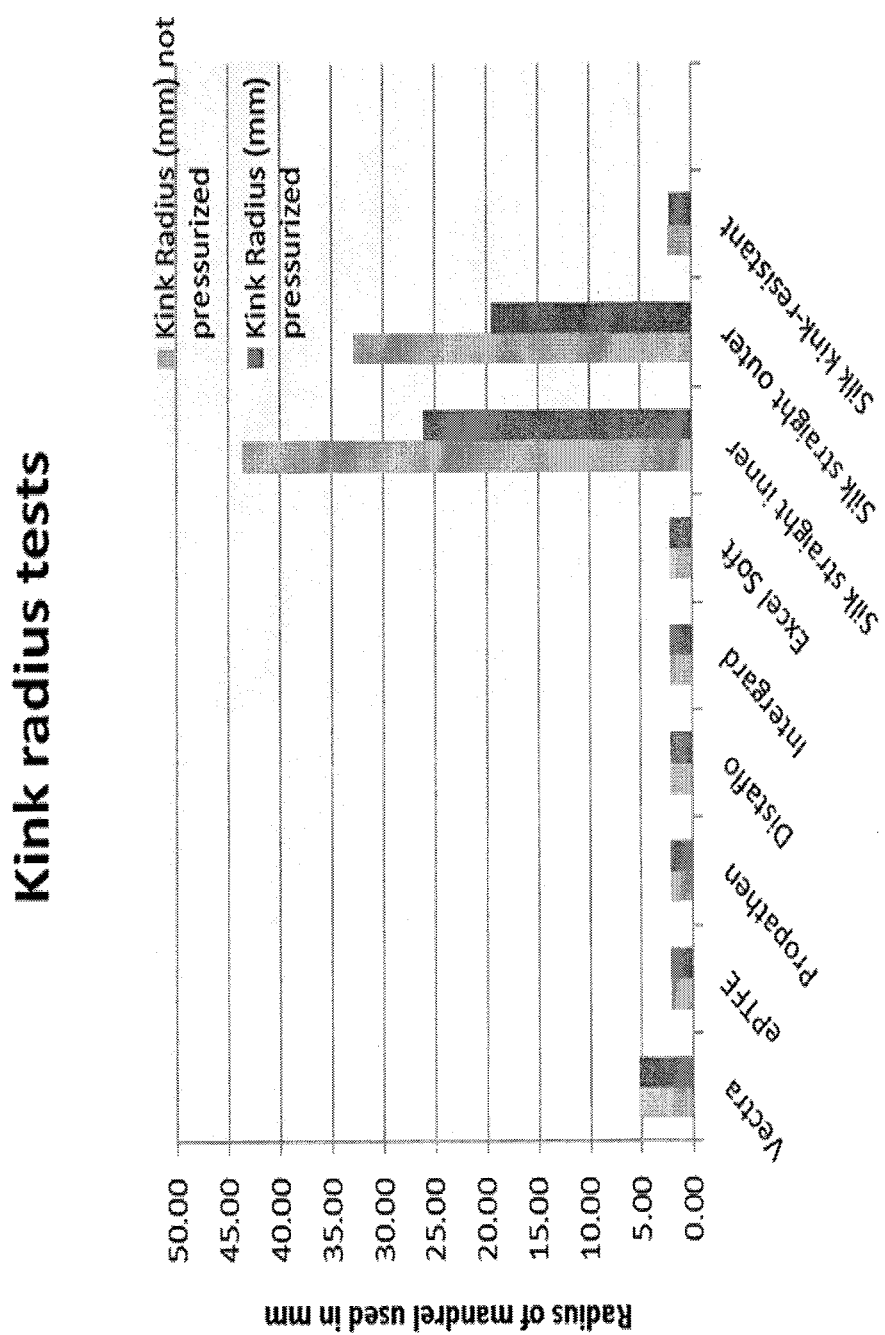
FIG. 8 shows the effect of the kink resistant helical design silk conduit. It is compared to the straight design silk conduit and to the main commercial competitor grafts on the market.

FIG. 8 show the effect of the helical design, much more kink resistant than the straight design, and compares the kink resistance of the different silk conduits to other commercial grafts on the market, both with or without pressure. The smaller the radius of the mandrel used, the better the kink resistance.

Example 6

Circumferential Stress/Strain Testing Protocol

Circumferential strength of the straight conduits was tested with a ring pulling test using an Instron and following the ANSI standards. For each measure, two stainless steel pins (1 mm diameter) were inserted in a small specimen ring cut from the tube to a length of at least its diameter. Each pin was gripped in one of the 2 Instron clamps. The pins were pulled apart at a constant rate of 50 mm/min with a 500N load cell. Each sample was stretched until complete failure of the ring. The length and the wall thickness of the rings were recorded for each specimen using precision Vernier calipers. The load/elongation results were only taken into account from the moment that all slack has been taken up. The stress was then calculated by dividing the resulting load by twice the wall thickness*the initial pin separation. The strain (no unit) corresponded to the elongation divided by the initial separation of the pins (4 mm). All tubes were left in PBS 1× at 37° C. at least 24 h before testing and they were tested in the hydrated state. The results are shown in FIGS. 9, 10A and B, and 11.

Figure 9:
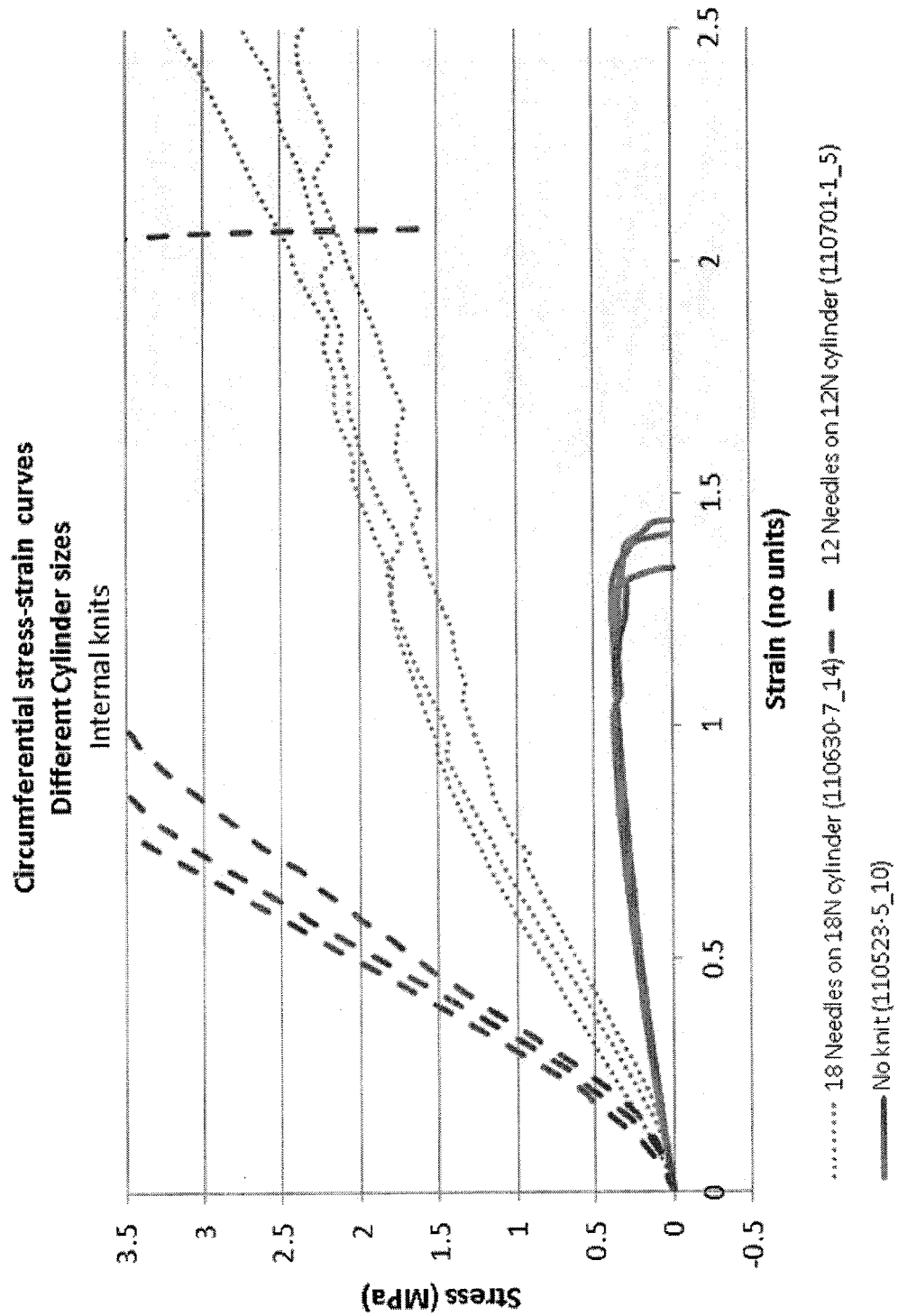
FIG. 9 shows the effect of the addition of a knitted layer to the mechanical properties of the conduit. The different patterns correspond to different sizes in the knitting structure: thick dotted curve is using a 12 needles knit, thin dotted line is using a 18 needles knit.
Figure 10A:
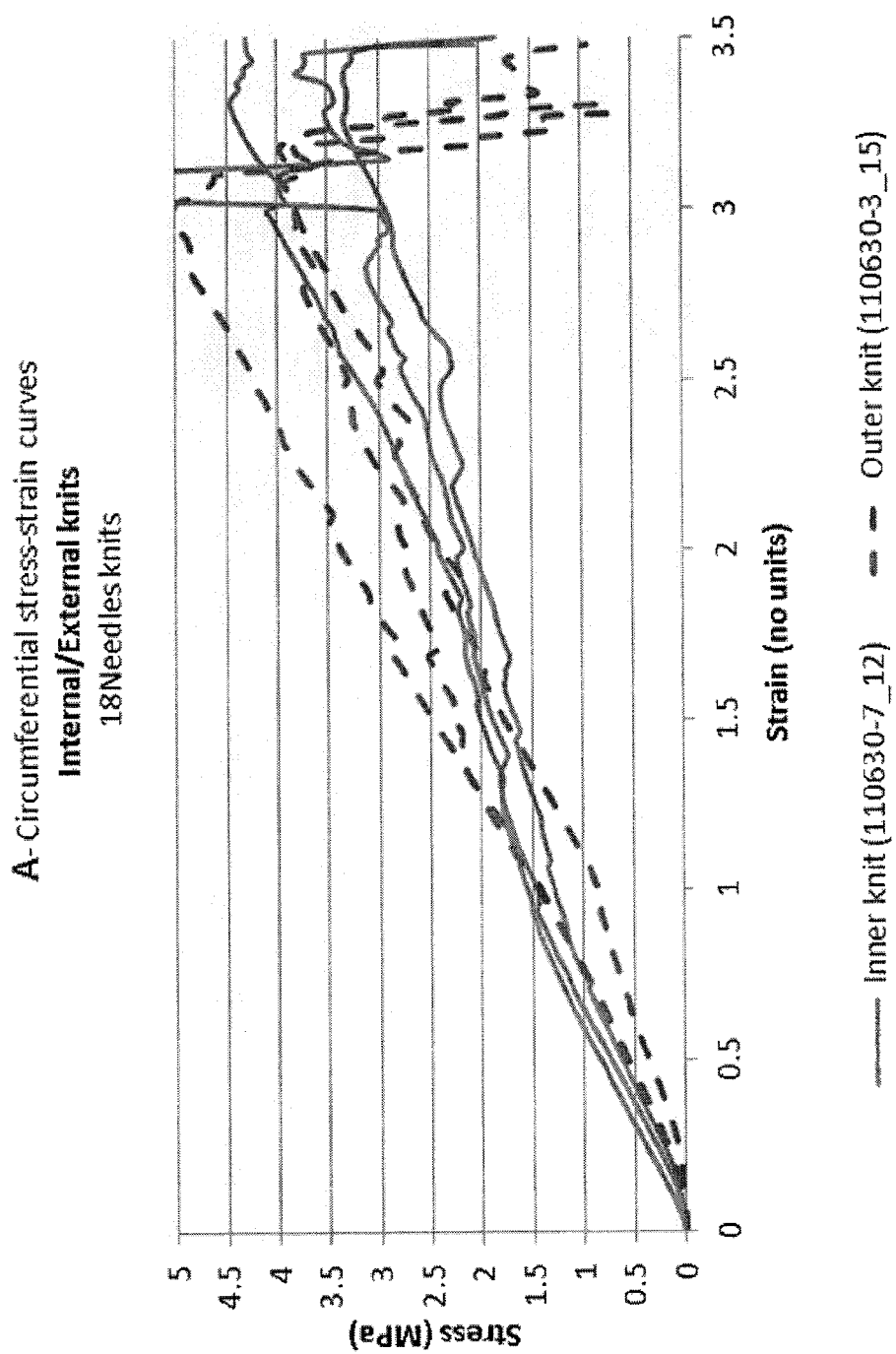
FIGS. 10 (A-B) show the effect of the external positioning of the knitted layer on the mechanical properties of the conduit. A—high pressures showing the maximum breaking stress/strain. B—low, physiological pressures.

FIG. 9 shows the effect of the addition of a knitted layer to the mechanical properties of the device. Ring pulling tests were carried out on various samples to compare their circumferential tensile stress/strain curves. The minimum, maximum and average curves are shown on the graph for each condition. Tubes consisting of a porous moulded fibroin matrix only (straight curves at the bottom). Composite tubes consisting of a porous moulded fibroin matrix and a knitted silk structure of various sizes (dotted curves). The different patterns correspond to different sizes in the knitting structure: thick dotted curve is using a 12 needles knit, thin dotted line is using a 18 needles knit.

Figure 10B:
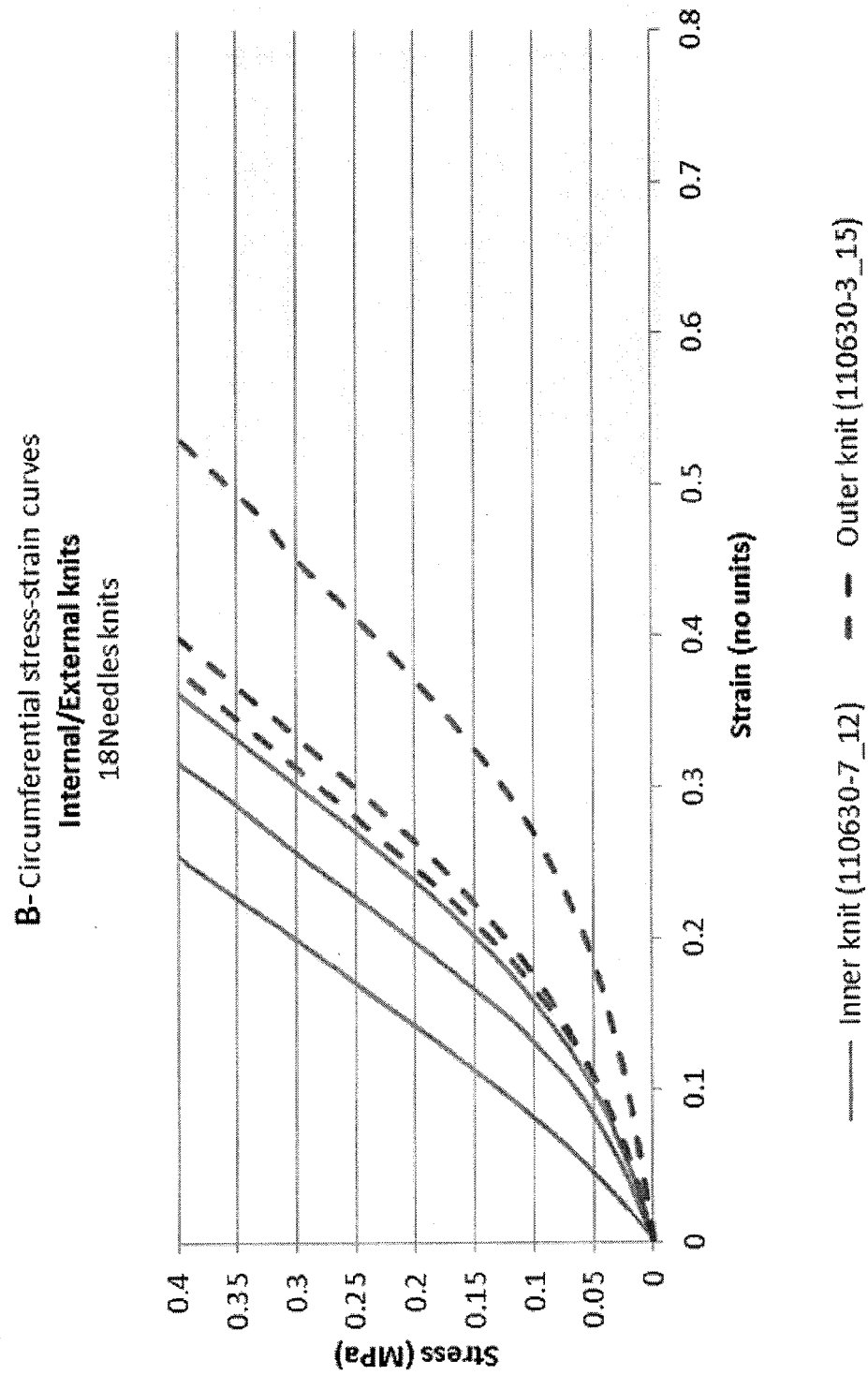

FIG. 10 (A-B) shows the effect of the external positioning of the knitted layer on the mechanical properties of the tube. Ring pulling tests were carried out on various samples to compare their circumferential tensile stress/strain curves. The minimum, maximum and average curves are shown on the graph for each condition. Tubes consisting of an internal knitted structure and an external porous moulded fibroin matrix (straight curves). Tubes consisting of an internal porous moulded fibroin matrix and an external knitted structure (dotted curves). A—High pressures showing the maximum breaking stress/strain. B—Low, physiological pressures.

Figure 11:
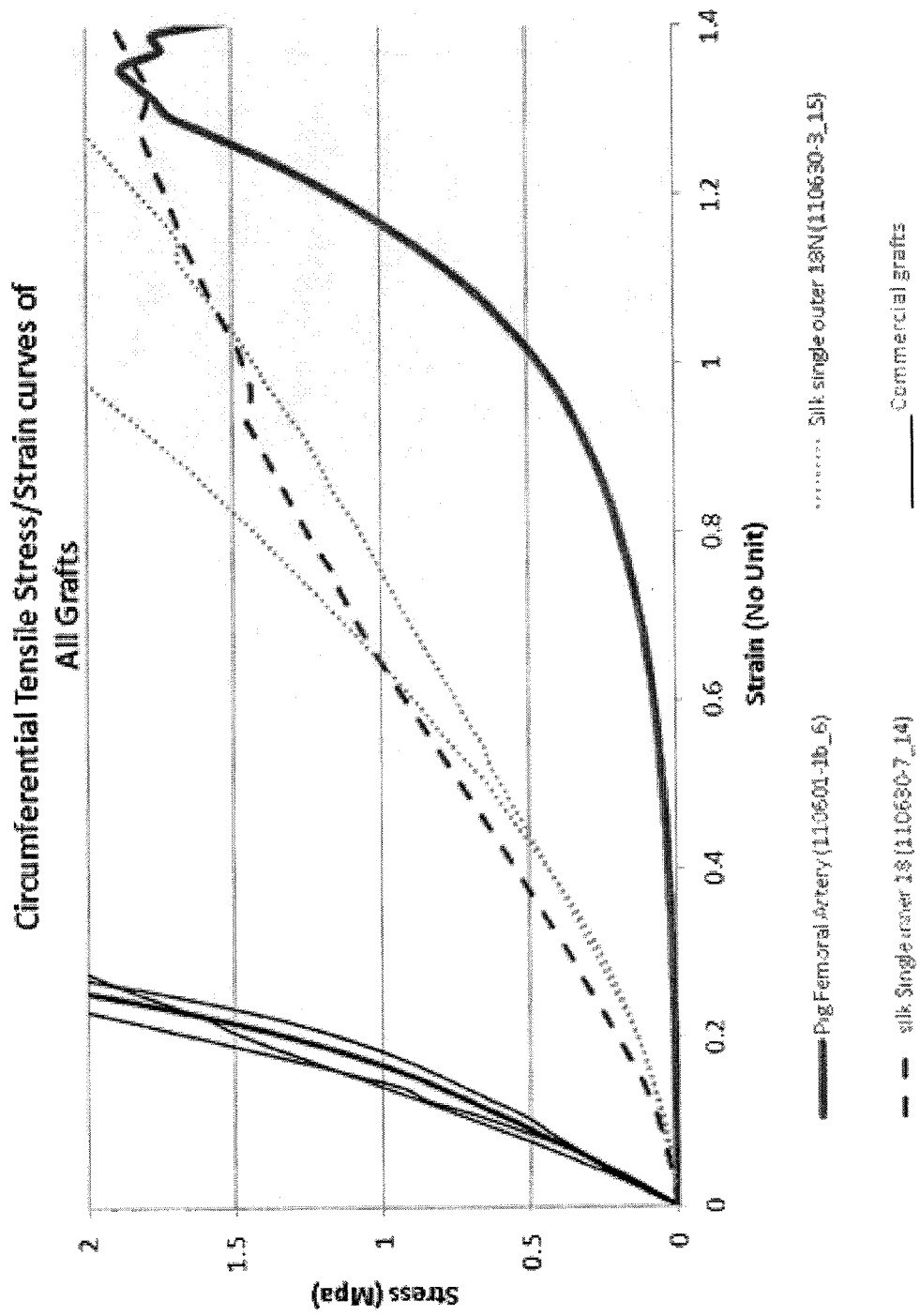
FIG. 11 shows a comparison of the stress/strain curves of pig femoral artery, commercial grafts and silk grafts. Commercially available PTFE and PET grafts (thin straight curves); silk grafts of the invention with external (dotted curves) or internal knit (dashed curve).

FIG. 11 shows a comparison of the stress/strain curves of pig femoral artery, commercial grafts and silk grafts. Ring pulling tests were carried out on various samples to compare their circumferential tensile stress/strain curves. The minimum, maximum and average curves are shown on the graph for each condition. Pig femoral artery (thick straight curve with lowest initial modulus). Commercially available PTFE and PET grafts (thin straight curves). Silk grafts of the invention with external (dotted curves) or internal knit (dashed curve).

Example 6

Use of the Vascular Graft

The device is provided in a sterilized condition (e.g. by beta-irradiation, by gamma irradiation or by autoclaving) and stored in PBS. The device is cut slightly longer than the size required by the surgeon and the device is placed at an anastomotic angle, reduced to its minimum. The device is sutured to the native vessel using appropriate sized suture and needle, for example with 5-0 or 6-0 sutures and CVII needles.

The silk used herein was obtained from China and India.

The invention claimed is:

1. A medical device comprising a tubular body and a long axis, wherein the tubular body comprises:
   (a) at least one layer of porous silk fibroin matrix; and
   (b) at least one layer of knitted silk fibres,
wherein the luminal layer is a layer of porous silk fibroin matrix,
and wherein one or more of the layers of knitted silk fibres is present, partially or completely, in an annulate, helical, threaded, spiral, grooved, corrugated or crimped form or profile.

2. A medical device as claimed in claim 1, wherein the innermost layer and/or the outermost layer of the tubular body are coated with an impermeable silk fibroin layer.

3. A medical device as claimed in claim 1, wherein the porous silk fibroin matrix is formed from regenerated or redissolved silk fibroin protein.

4. A medical device as claimed in of claim 1, wherein the silk fibroin or silk fibres are obtained from cocoon silks or silk filaments from the domesticated Mulberry Silkworm (*Bombyx mori*), or from cocoon silks or silk filaments from non-mulberry silk worms or wild (non-domesticated) silk worms.

5. A medical device as claimed in of claim 1, wherein the device is kink-resistant.

6. A medical device as claimed in of claim 1, wherein one or more of the layers of porous silk fibroin matrix is moulded, partially or completely, into an annulate, helical, threaded, spiral, grooved, corrugated or crimped form or profile.

7. A medical device as claimed in claim 1, wherein one or more silk threads or sutures are engaged in the grooves of the annulate, helical, threaded, spiral, grooved, corrugated or crimped form or profile on the outer side of the knitted layer(s).

8. A medical device as claimed in of claim 1, wherein the tubular body comprises:
   (a) a luminal layer of porous silk fibroin matrix; and
   (b) two layers of knitted silk fibres, embedded in or coated with a porous silk fibroin matrix.

9. A medical device as claimed in claim 1, wherein the proteins in one or more layers of the device are cross-linked.

10. A medical device as claimed in claim 1, wherein one or more layers are wholly or partially inter- or intra-cross-linked to make the layer(s) and/or the device substantially non-degradable or substantially non-biodegradable.

11. A medical device as claimed in claim 1, wherein the porous fibroin matrix has pores of between 10 μm and 50 μm in diameter.

12. A medical device as claimed in claim 1, wherein the device is an arteriovenous (AV) graft for haemodialysis, a vascular graft, a bifurcation graft or an anastomosis device.

13. A method of replacing a diseased artery or vein in a patient comprising removing all or part of a diseased artery or vein in that patient and replacing all or part of the diseased artery or vein with a vascular graft, a bifurcation graft or an anastomosis device as claimed in claim 12.

14. A method of treating a patient with coronary heart disease, comprising replacing all or part of one or more of the patient's coronary arteries or veins with a vascular graft, a bifurcation graft or an anastomosis device as claimed in claim 12.

15. A method of preparing a patient for haemodialysis, comprising inserting an arteriovenous (AV) graft as claimed in claim 12 between one of the patient's arteries and one of the patient's veins.

16. A method of haemodialysis, comprising the steps:
   (i) extracting blood from a patient through an arteriovenous (AV) graft as claimed in claim 12,
   (ii) dialysing the extracted blood, and optionally
   (iii) returning the dialysed blood to the patient.

17. A process of manufacturing a medical device as claimed in claim 2 comprising the step of forming a tubular body comprising:
   (a) a layer of porous silk fibroin matrix; and
   (b) a layer of knitted silk fibres,
wherein the luminal layer is a layer of porous silk fibroin matrix,
and wherein one or more of the layers of knitted silk fibres is present, partially or completely, in an annulate, helical, threaded, spiral, grooved, corrugated or crimped form or profile.

18. A process of manufacturing a medical device as claimed in claim 17, comprising the steps:
   (i) inserting one or more tubular layers of knitted silk fibres onto a cylindrical former;
   (ii) applying a coating of regenerated or redissolved silk fibroin solution onto the knitted layer(s) and allowing the coating to set;
   (iii) removing the coated knitted layer(s) from the former;
   (iv) inserting the coated knitted layer(s) into a mould,
   (v) injecting regenerated or redissolved silk fibroin into the mould between a centered former and the set knitted layer, and allowing the silk fibroin to set,
such that a tubular body is formed in the mould comprising concentric layers of one or more layers of knitted silk fibres and one or more layers of porous silk fibroin matrix.

19. A process of manufacturing a medical device as claimed in claim 17, comprising the steps:

(i) inserting one or more tubular layers of knitted silk fibres onto a former having a annulate, helical, threaded, spiral, grooved, corrugated or crimped form or profile;

(ii) winding a silk thread or suture over the knitted silk fibre layer(s) at a tension such that the silk thread or suture and silk fibre layer(s) engage within the grooves of the former;

(iii) applying a coating of regenerated or redissolved silk fibroin solution onto the knitted layer(s);

(iv) allowing the coating of regenerated or redissolved silk fibroin solution to dry;

(v) removing the coated knitted layer(s) from the former;

(vi) inserting the coated knitted layer(s) into a mould;

(vii) injecting regenerated or redissolved silk fibroin into the mould, and allowing the silk fibroin to set, such that a tubular body is formed in the mould comprising concentric layers of one or more layers of knitted silk fibres and one or more layers of porous silk fibroin matrix.

20. A process as claimed in claim 17, wherein the process additionally comprises one or more of:

(a) freezing the moulded device;
(b) gelling the proteins in the moulded device;
(c) freezing the proteins of the moulded device;
(d) treating the moulded device with an alcohol; and
(e) cross-linking the proteins of the moulded device.

\* \* \* \* \*